(12) United States Patent
Tuan et al.

(10) Patent No.: US 6,967,255 B2
(45) Date of Patent: Nov. 22, 2005

(54) PHENANTHRENE COMPOUNDS

(75) Inventors: Chi-Shen Tuan, Hsinchu (TW); Zong-Wei Tsai, Kaohsiung (TW); S-Sling Hsu, Hsinchu (TW); Han-Bin Cheng, Kaohsiung (TW); Yu-Fen Cheng, Hsinchu (TW); Shinn-Jen Chang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 131 days.

(21) Appl. No.: 10/774,103

(22) Filed: Feb. 6, 2004

(65) Prior Publication Data

US 2005/0176952 A1 Aug. 11, 2005

(51) Int. Cl.[7] .................. C07C 49/215; C07C 50/32

(52) U.S. Cl. .............. 552/298; 428/917; 428/704; 428/446; 428/448; 428/690; 552/299; 552/295; 552/292; 552/544

(58) Field of Search ............... 428/690, 917, 428/704, 446, 448; 313/504, 506; 552/292, 552/295, 298, 299

(56) References Cited

U.S. PATENT DOCUMENTS 5,763,636 A * 6/1998 Kreuder et al. ............... 558/46
6,268,072 B1 * 7/2001 Zheng et al. ............... 428/690

FOREIGN PATENT DOCUMENTS

TW 2003-55276 2/2003 ............. 13/62

OTHER PUBLICATIONS

Ayats et al, AN 2003:784844 HCAPLUS, DN 139:395638; Abstract of Journal of Organic Chemistry (2003), 68(22), 8715-8718.*
Van Ornum et al, AN 1997:764120 HCAPLUS, DN 128: 114621; Abstract of Journal of the Chemical Society, Perkin Transactions 1: Organic and Bio-Organic Chemistry (1997), (22), 3471-3478.*
Camps et al, AN 1995:512496 HCAPLUS, DN 123:55418; Abstract of Synthetic Communications (1995), 25(9), 1287-93.*
Kubiak et al, AN 1985:541178 HCAPLUS, DN 103: 141178; Abstract of Tetrahedron Letters (1985), 26 (18), 2163-6.*

* cited by examiner

*Primary Examiner*—Sabiha N. Qazi
(74) *Attorney, Agent, or Firm*—Thomas, Kayden, Horstemeyer & Risley

(57) ABSTRACT

A phenanthrene compound represented by the formula (I):

Formula (I)

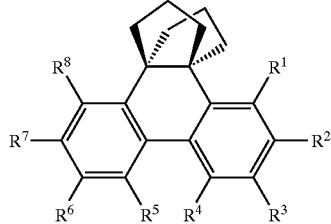

in which, $R^1$, $R^2$, $R^3$, $R^4$, $R^5$, $R^6$, $R^7$, and $R^8$ are identical or different and may each be hydrogen, halogen, $C_{1-6}$ alkyl, $C_{1-6}$ alkoxy, or a conjugated group. The phenanthrene compound has a polycyclic structure and semiconductor properties including electron transfer, electroluminescence, and photoluminescence.

10 Claims, 2 Drawing Sheets

PHENANTHRENE COMPOUNDS

BACKGROUND OF THE INVENTION

1. Field of the Invention

The present invention relates to a compound, and particularly a phenanthrene compound having a polycyclic structure and semiconductor characteristics including electron transfer, electroluminescence, and photoluminescence.

2. Description of the Related Art

Molecular material used in organic light-emitting diodes (OLED), organic electroluminescence (EL) devices, or photovoltaic devices contains a conjugated molecule structure having double bonds alternating with single bonds to form $sp^2$ hybrid orbitals such that the structure tends to form a plane. The conductivity of the conjugated molecule is accomplished by the transfer of the unpaired electrons through the $\pi$-$\pi^*$ delocalized conjugated bonds formed by the Pz orbitals of the carbon atoms. For such conjugated molecules, there is an energy gap ($E_g$) between HOMO (the highest occupied molecular orbital) and LUMO (the lowest unoccupied molecular orbital), and this provides the molecular material with semiconductor properties. The emitted light color depends on the energy gap. Nevertheless, due to the plane structure, the molecules tend to stack on each other and crystallize during film forming for applications, resulting in the device failure.

U.S. Pat. No. 6,268,072 (Eastman Kodak, 2001) discloses an electroluminescent polymer composition comprising a copolymer of adamantine, phenylene, and phenylanthracene. WO 02/26856 (CDT, 2002) discloses a polymer having a cyclic structural monomeric unit comprising a 5-member ring between a pair of phenyl rings, in which the two phenyl rings distort each other in the range of 50 to 750 and have a blue shift effect. U.S. Pat. No. 5,763,636 (Hoechst, 1998) discloses an electroluminescent polymer having a spiro-PF new structure. EP 1074600 (Sumitomo, 2001) discloses a copolymer having cyclic molecular moieties. JP Kokai No. 2003-55276 (Sony, 2003) discloses a phenanthrene electroluminescent material and a method of producing the same, in which the disclosed blue-light-emitting electroluminescent phenanthrene molecule and co-compound thereof are small molecules, which, upon reacting with other molecules, result in various blue-light-emitting electroluminescent molecules.

The techniques mentioned above attempt to prevent molecules from stacking on each other by a soft alkane chain, a distortion of the pair of phenyl rings in the main chain, or a norbornane group on the phenanthrene molecule, but only limited effect is achieved.

Hence, there is still a need for conjugated molecular material avoiding stacking during film formation for application in OLED, EL, photovoltaic devices, and the like.

SUMMARY OF THE INVENTION

Accordingly, an object of the invention is to provide a novel phenanthrene compound with a polycyclic conjugated structure as a main structure, in which the delocalized orbitals provide electron/hole transfer, good heat resistance, and structural stability. An organic semiconductor material with specific energy gap or high electron/hole transfer efficiency can be synthesized from the phenanthrene compound with other conjugated compounds. Furthermore, when the compound is used as a luminescent layer in a device, molecule stacking is avoided due to the special structure with two special stereo cyclopentane rings which prevent intermolecular aggregation.

To achieve the object of the present invention, the phenanthrene compound of the present invention is represented by the formula (I):

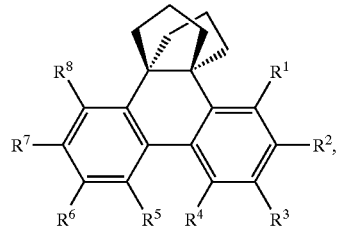

Formula (I)

in which, $R^1$, $R^2$, $R^3$, $R^4$, $R^5$, $R^6$, $R^7$, and $R^8$ are identical or different and each may be hydrogen, halogen, $C_{1-6}$ alkyl, $C_{1-6}$ alkoxy, or a conjugated group.

Although the present invention and conventional techniques both involve a phenanthrene main structure, the two special stereo cyclopentane rings in the phenanthrene compound prevent the two phenyl rings in the main chain from approaching each other, such that molecule stacking is avoided and the stability of the molecular structure is maintained, as shown in the computer-simulated molecular arrangement view in FIG. 1.

The phenanthrene compound of the present invention has a polycyclic structure and semiconductor properties including electron transfer, electroluminescence, and photoluminescence and can be advantageously applied in, for example, CD/DVD dyes, OLED devices, EL devices, photovoltaic devices and sensors.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
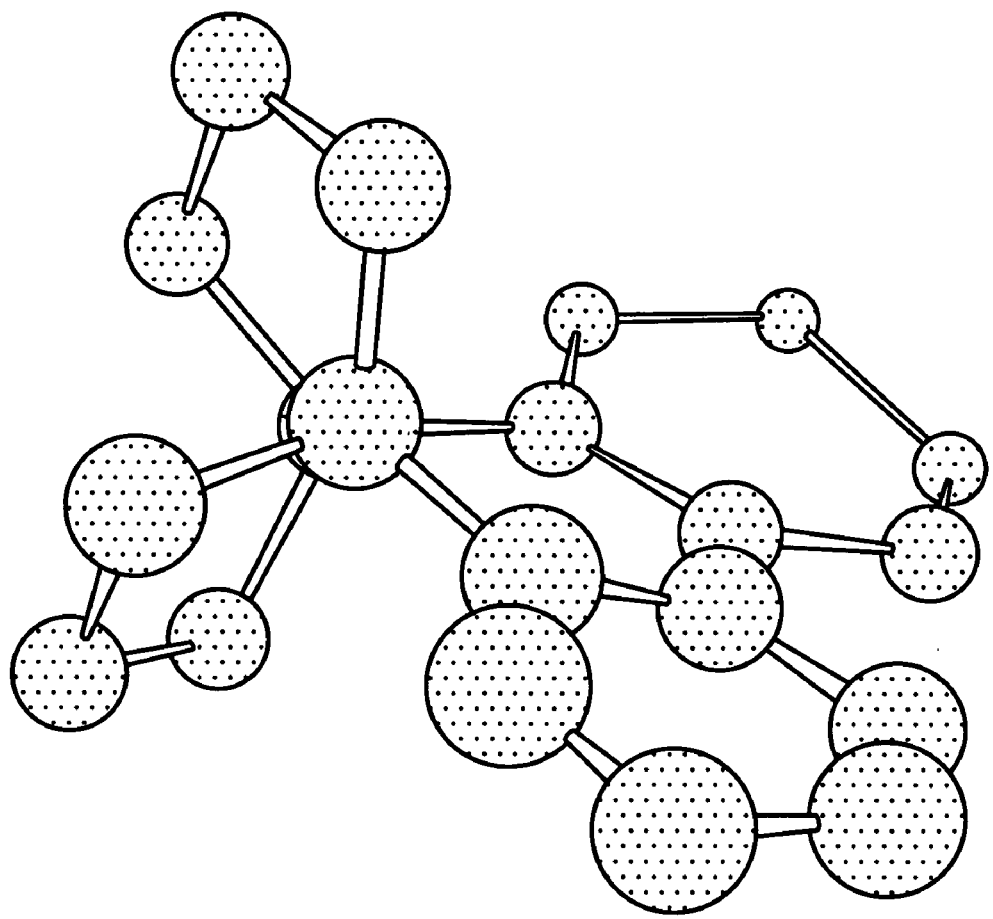
FIG. 1 is a computer-simulated molecular arrangement stereo view of the phenanthrene compound of one example of the present invention.
Figure 2:
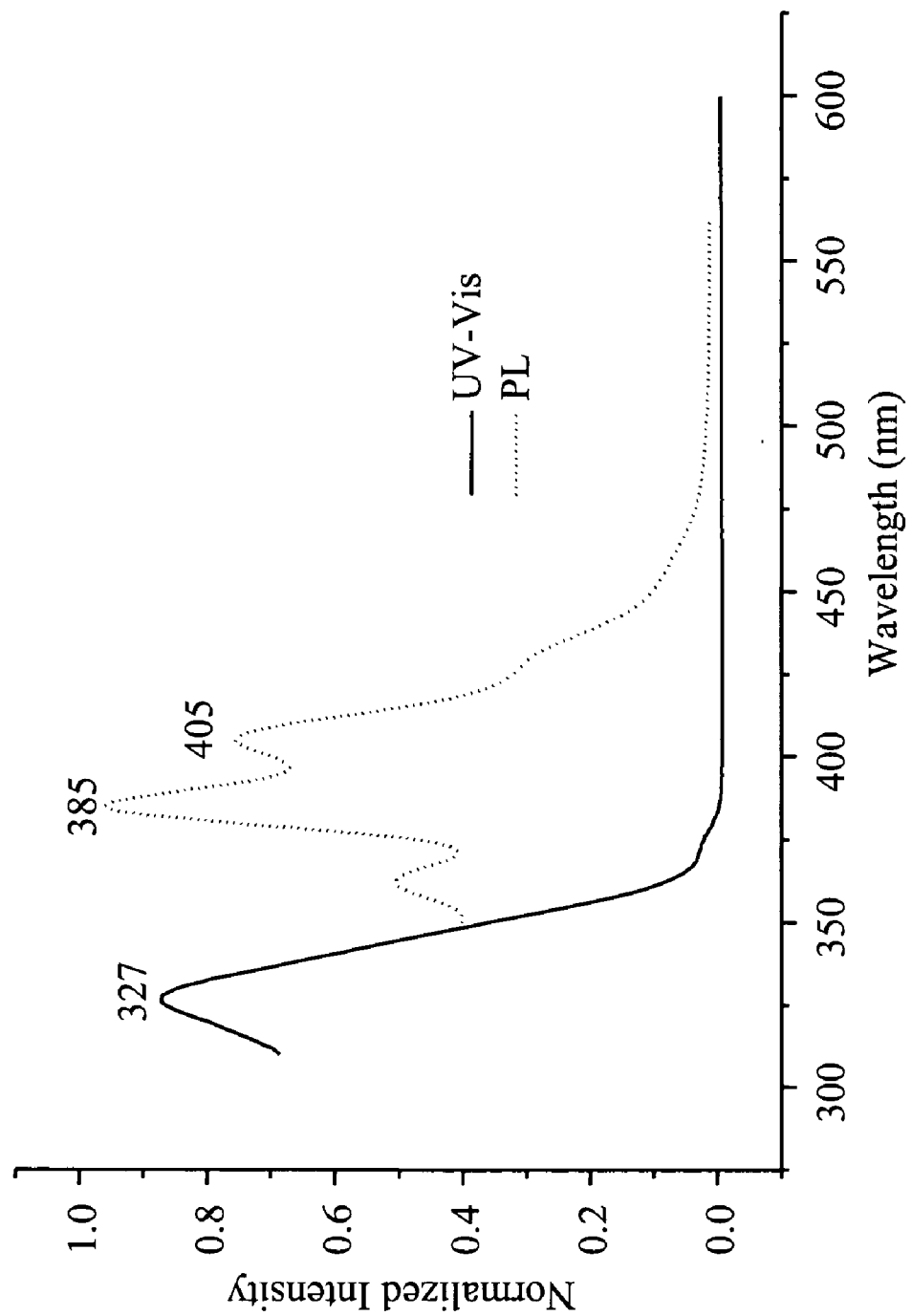
FIG. 2 shows a UV-Visible light absorption spectrum and a photoluminescence (PL) spectrum of the phenanthrene compound 3 obtained from Example 3 according to the present invention.

The phenanthrene compound of the present invention is represented by the formula (I):

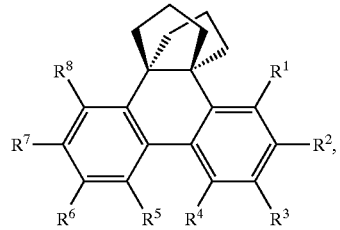

Formula (I)

which is a novel compound having two propylene groups (i.e. two trimethylene groups) bonded to the two carbon atoms numbered 9 and 10 of the phenanthrene compound. The derivative based on this structure is also novel. In formula (I), $R^1$, $R^2$, $R^3$, $R^4$, $R^5$, $R^6$, $R^7$, and $R^8$ are defined as described above, that is, identical or different and may be hydrogen, halogen, $C_{1-6}$ alkyl, $C_{1-6}$ alkoxy, or a conjugated group. Preferably, $R^1$, $R^3$, $R^4$, $R^5$, $R^6$, and $R^8$ are hydrogen, $R^2$ and $R^7$ are substituted or unsubstituted phenyl, a substituted or unsubstituted heterocyclic group, substituted or unsubstituted polycyclic phenyl, or a substituted or unsubstituted polycyclic heterocyclic group. In the polycyclic structure of the phenanthrene compound of the present invention, two trimethylene groups are bonded to phenanthrene such that the two end carbon atoms of each trimethylene group are linked to carbon atoms 9 and 10 of phenanthrene respectively, exhibiting a fused ring system comprising two cyclopentanes and one ring from phenanthrene, having two atoms and one covalent bond in common, as shown in Formula (I). The two phenyl rings in this phenanthrene compound perform electron transfer and the special stereo two-cyclopentane structure effectively prevents molecule aggregation, so that the molecule stacking is avoided and light emitting stability is improved. When one of $R^1$, $R^2$, $R^3$, $R^4$, $R^5$, $R^6$, $R^7$, and $R^8$ is a conjugated bond, such as a substituted or unsubstituted phenyl, substituted or unsubstituted heterocyclic group, substituted or unsubstituted polycyclic phenyl, or substituted or unsubstituted polycyclic heterocyclic group, the length of conjugated bonding of the entire molecule is increased, such that electron transfer and energy gap regulation for the molecules are improved. Examples of the phenyl, heterocyclic group, polycyclic phenyl, and polycyclic heterocyclic group mentioned are, but are not limited to, (referred to as Formula (II)):

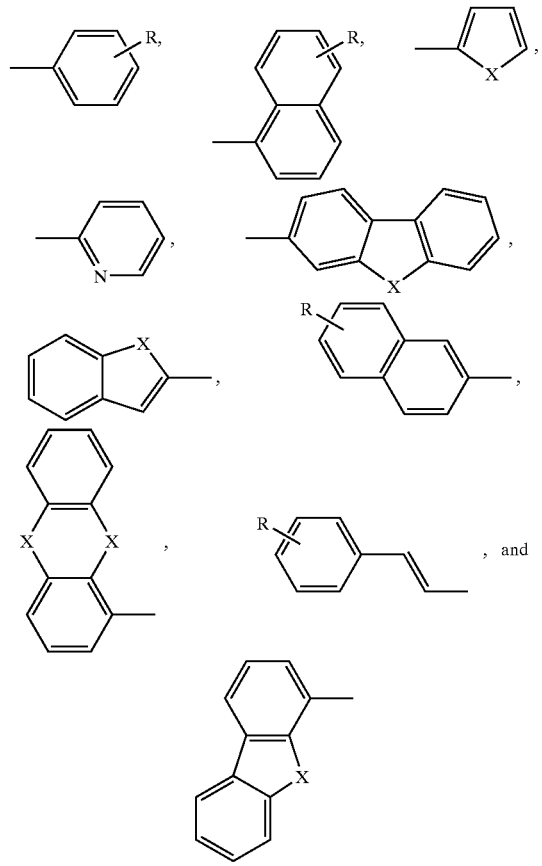

wherein R is $C_{1-20}$ alkyl or $C_{1-20}$ alkoxy, and X is S, O, or N. R is preferably $C_{1-6}$ alkyl or $C_{1-6}$ alkoxy.

In one example according to the present invention, $R^2$ and $R^7$ are each Formula (II) and $R^1$, $R^3$, $R^4$, $R^5$, $R^6$, and $R^8$ are hydrogen, whereby the resulting phenanthrene compound emits fluorescent light at a wavelength of about 350–500 nm. Electroluminescent emission of blue, red, green, or various colors can be obtained by incorporating other suitable substances into the phenanthrene compound or by co-synthesis of the phenanthrene compound and a compound having a different energy gap.

The following reaction scheme illustrates the preparation of the phenanthrene compound according to the present invention:

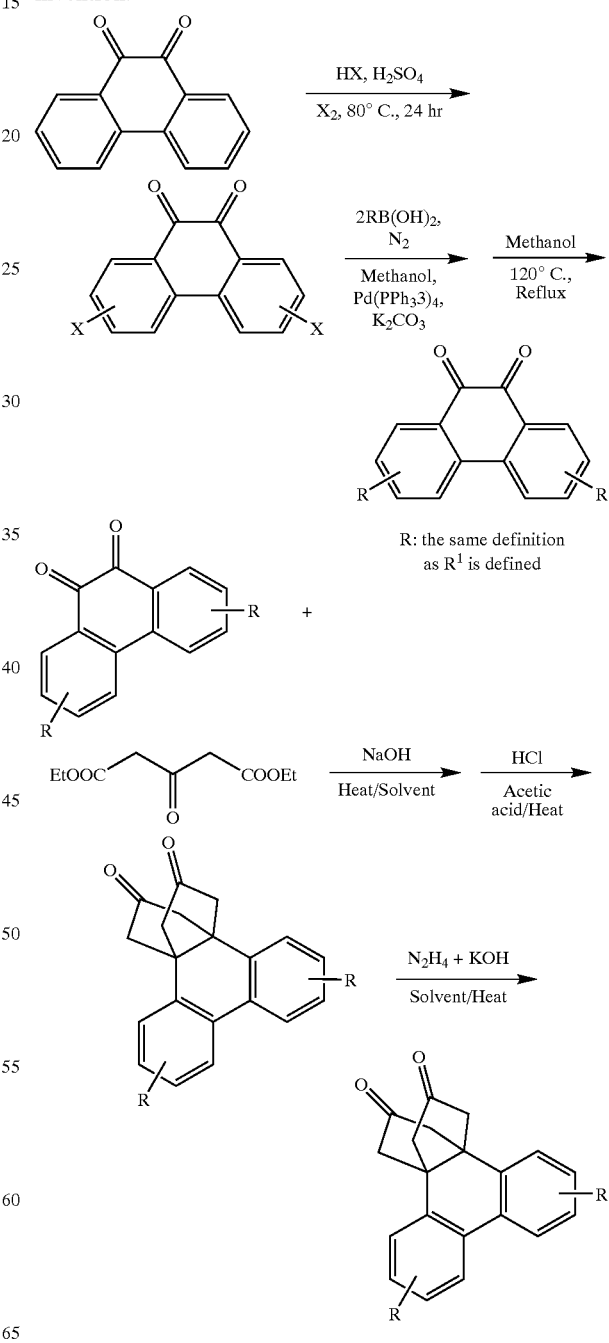

In the above reaction scheme, phenanthrene-9,10-diketone is dissolved in proper hydrogen halide and $H_2SO_4$, and heated to 80° C., and a small amount of halogen is added slowly, after which the mixture is allowed to react for 24 hours. After precipitation and filtration, dihalophenanthrene-9,10-diketone is obtained. Under nitrogen, sodium carbonate aqueous solution, Pd(PPh$_3$)$_4$ as a catalyst, and Aliquat 336 as a phase transfer catalyst are added to a solution of alkyl or phenyl boric acid and the obtained dihalophenanthrene-9,10-diketone is refluxed in toluene to reaction at 120° C. for 12 hours, giving di-R group-phenanthrene-9,10-diketone as a white solid. Di-R-group-phenanthrene-9,10-diketone and 2 equivalents of diethyl 1,3-acetonedicarboxylate are heated to react in the presence of NaOH. After complete reaction, the reaction mixture is neutralized with HCl solution, giving precipitates. The precipitates are dissolved in acetic acid and allowed to react at an elevated temperature, then, neutralized with sodium carbonate aqueous solution, precipitated, and filtered, giving a compound having a two cyclopentanone fused ring structure. The compound and 2 equivalents of N$_2$H$_4$ are heated in a solvent and react to substitute the ketone group with two hydrogen atoms, forming the novel phenanthrene compound of the present invention.

Alternatively, the phenanthrene compound of the present invention can be prepared as illustrated in the following reaction scheme:

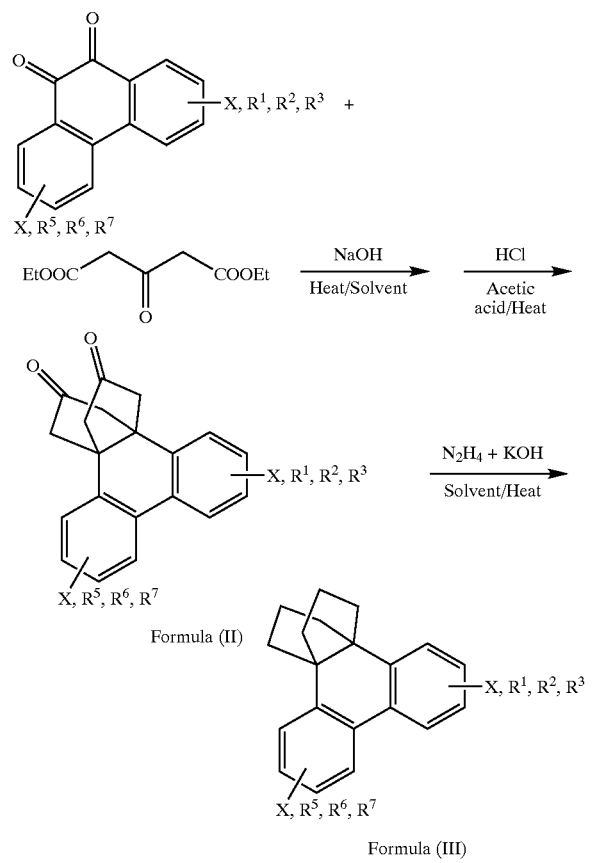

Formula (III)

X is a halo group, and R$^1$, R$^2$, R$^3$, R$^5$, R$^6$, and R$^7$ are defined as above Thus, dihalophenanthrene-9,10-diketone and 2 equivalents of diethyl 1,3-acetonedicarboxylate in a solvent are heated to react in the presence of NaOH. After the reaction is completed, the reaction mixture is neutralized with HCl solution, giving precipitates. The precipitates are dissolved in acetic acid and allowed to react at an elevated temperature, then neutralized with sodium carbonate aqueous solution, precipitated, and filtered, giving a compound of Formula (II). The compound of Formula (II) and 2 equivalents of N$_2$H$_4$ in a solvent are heated and react to substitute the ketone group with two hydrogen atoms, forming a compound of Formula (III).

The phenanthrene compound having other specific substituent(s) of the present invention can be further produced through Suzuki Coupling Reaction from the compound of Formula (III). The following reaction scheme is shown as an example:

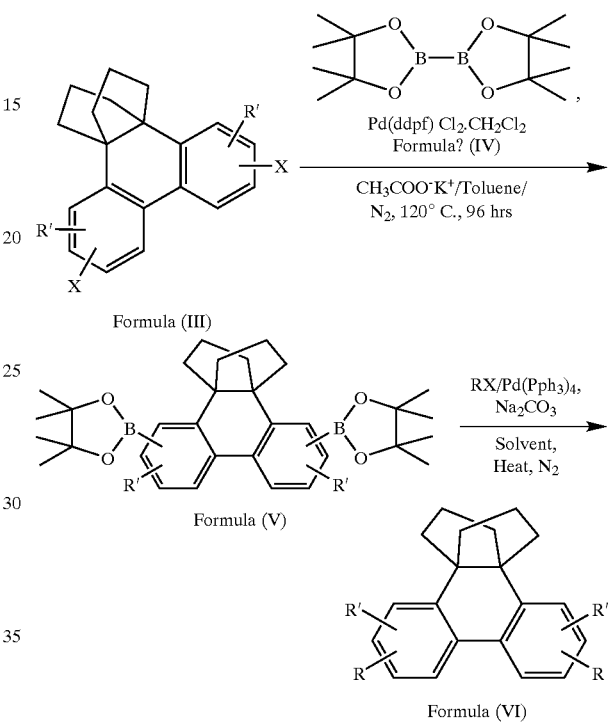

R: the same definition as R$^1$ is defined
X: halo group

Compound of Formula (III) and 2 equivalents of diborate compound of Formula (IV) in a solvent are reacted in the presence of CH$_3$COOK and Pd(dppf)Cl$_2$ as a catalyst, giving a compound of Formula (V). Under nitrogen, the compound of Formula (V) and 2 equivalents of RX in a solvent are heated to react with Pd(PPh$_3$)$_4$ and sodium carbonate as a catalyst, resulting in a compound of Formula (VI) having the R group. When such method is used to produce the phenanthrene compound of the present invention, R group is preferably a substituted or unsubstituted phenyl, substituted or unsubstituted polycyclic phenyl, or substituted or unsubstituted polycyclic heterocyclic group.

Alternatively, the following reaction scheme is shown as an example:

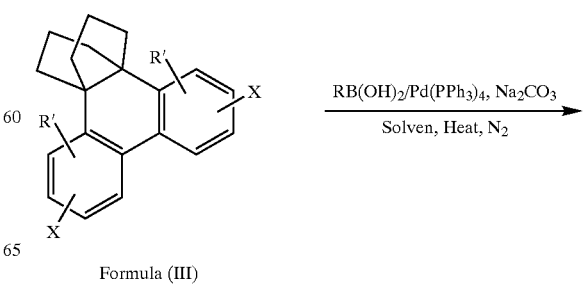

Formula (III)

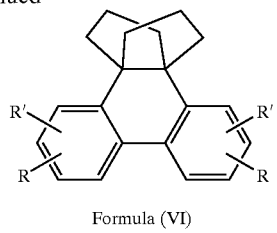

Formula (VI)

Under nitrogen, the compound of Formula (III) and 2 equivalents of RB(OH)$_2$ in a solvent are heated to react with Pd(PPh$_3$)$_4$ and sodium carbonate as a catalyst, resulting in a compound of Formula (VI) having the R group. When such method is used to produce the phenanthrene compound of the present invention, R group is preferably a substituted or unsubstituted phenyl, substituted or unsubstituted polycyclic phenyl, or substituted or unsubstituted polycyclic heterocyclic group.

The phenanthrene compound of the present invention is an organic semiconductor conjugated molecule suitable for use in photoelectric or semiconductor devices. An organic photoelectric device can be manufactured by vapor deposition of a hole transferring layer over the ITO substrate, a layer of the phenanthrene compound of the present invention over the hole transferring layer, an electron transferring layer over the phenanthrene compound layer, and a metal layer as a cathode over the electron transferring layer. By the similar method, an organic light-emitting diode (OLED), organic electro luminescence (EL) device, photovoltaic device, CD/DVD dye, OLED device, EL device, photovoltaic device or sensor can be produced.

EXAMPLES

Example 1

Synthesis of 9,10:9,10-bis(trimethylene)-2,7-dibromo-9,10-dihydrophenanthrene 3 grams of phenanthrene-9,10-diketone (manufactured by Aldrich Co., 95%) was dissolved in 60 ml HBr and 20 ml H$_2$SO$_4$, and heated to 80° C., and a small amount of Br$_2$ (manufactured by ACROS Co.) was added slowly, after which the mixture was allowed to react for 24 hours. After precipitation and filtration, dibromophenanthrene-9,10-diketone was obtained at a yield of more than 90%.

2 grams of NaOH and 200 ml methanol was mixed and heated to about 60° C. After NaOH was dissolved completely, 3 grams of dibromophenanthrene-9,10-diketone and 4 grams of diethyl 1,3-acetonedicarboxylate (manufactured by ACROS Co., 95%) were added and the temperature was maintained at 60° C. After 36 hours of reaction, 10% HCl aqueous solution was added to the reaction mixture for neutralization, and then the mixture precipitated and filtered. The precipitate collected was dissolved by acetic acid, 300 ml 10% HCl aqueous solution was added, and reaction tookplace for 18 hours at an elevated temperature. Then, acetic acid and water were removed, and the product neutralized with sodium hydrogen carbonate aqueous solution, precipitated, and filtered, giving Reactant 1 at a yield of 17%.

The following reaction scheme illustrates the preparation of Reactant 1:

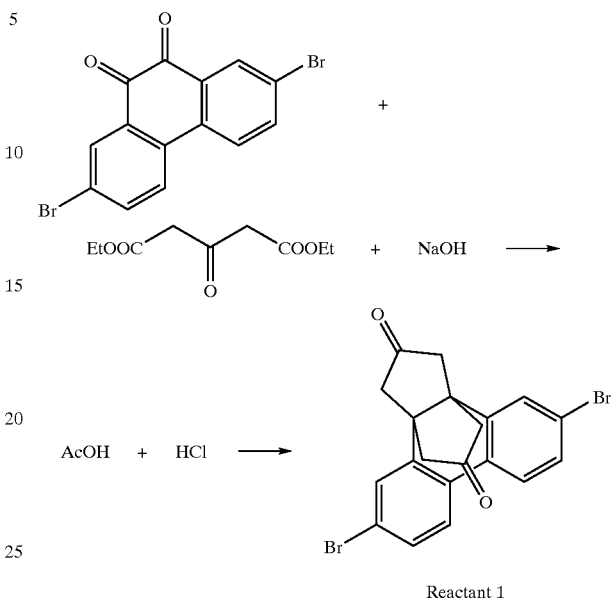

Reactant 1

3 grams of Reactant 1 and 150 ml ethylene glycol were mixed, 0.5 grams of N$_2$H$_4$ (manufactured by Lancaster Co., 98%) was added, and the resulting mixture was stirred for 10 minutes, then 0.5 grams of KOH was added, and heated to about 180° C. for reaction. After 15 hours, the reactionmixture was cooled to room temperature and diluted with water, resulting in a white solid product (Compound 1), at a yield of 61%, herein referred as 9,10:9,10-bis(trimethylene)-2,7-dibromo-9,10-dihydrophenanthrene. This Compound 1 is the novel phenanthrene compound of the present invention, and is also a mediate for the synthesis of various phenanthrene compounds of the present invention. $^1$H NMR (CDCl$_3$): δ (ppm) about 1.40 (m, 2H), about 1.70 (m,2H), 1.88–1.96(m, 4H), 2.10–2.16(m, 4H), 7.23–7.26(m, 2H), 7.23–7.26(m, 2H), 7.92(s, 2H).

The following reaction scheme illustrates the preparation of Compound 1:

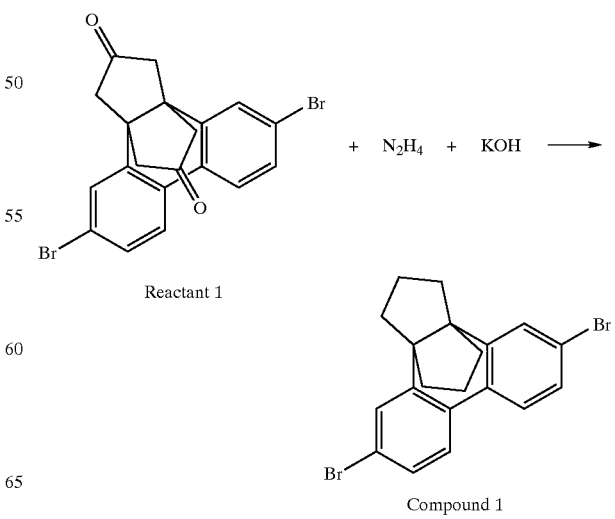

Example 2

Synthesis of 9,10:9,10-bis(trimethylene)-2,7-bis-2-naphthalyl-9,10-dihydrophenanthrene In a nitrogen atmosphere, 1 ml 2M sodium carbonate aqueous solution and Pd(PPh$_3$)$_4$ as a catalyst were added to a solution of 0.42 grams of 2-naphthaleneboronic acid (manufactured by Lancaster Co., 97%) and 0.5 grams of Compound 1 in 40 ml toluene and the product refluxed to reaction at 120° C. for 12 hours, giving Compound 2 as a white solid at a yield of 39%. Compound 2 is the novel phenanthrene compound of the present invention. $^1$H NMR (CDCl$_3$): δ (ppm) 1.53 (m, 2H), about 1.70 (m, 2H), 2.21–2.26 (m, 4H), 2.07–2.14(m, 4H), 7.26–7.54(m, 2H), 7.91–8.01(m, 16H), 8.25(s,1H). UV: λ$_{max}$ 312 nm. PL: λ$_{max}$ 416 nm.

The following reaction scheme illustrates the preparation of Compound 2:

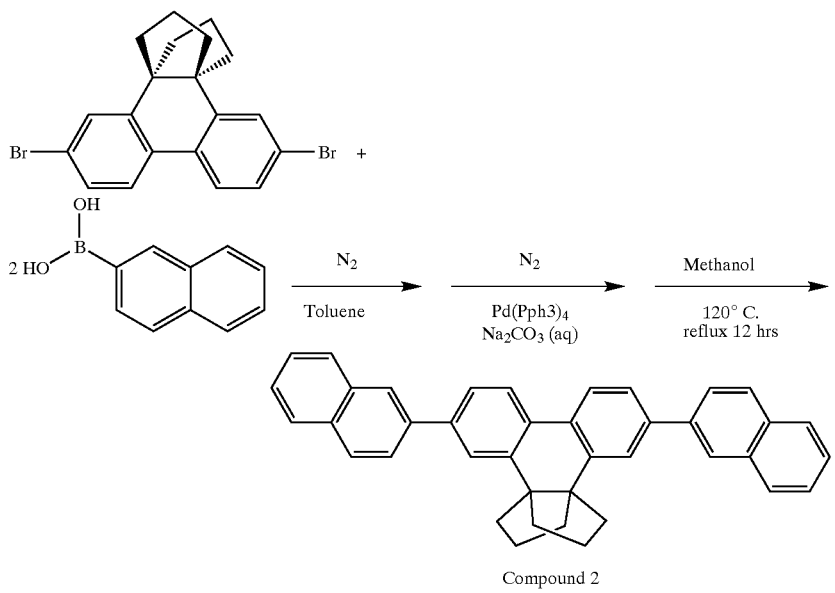

Compound 2

Example 3

Synthesis of 9,10:9,10-bis(trimethylene)-2,7-bis(4-ethoxyphenyl)-9,10-dihydrophenanthrene Under nitrogen, 1 ml 2M sodium carbonate aqueous solution and Pd(PPh$_3$)$_4$ as a catalyst were added to a solution of 0.40 grams of 4-ethoxyphenylboronic acid (manufactured by Aldrich Co.) and 0.5 grams of Compound 1 in 40 ml toluene and the product refluxed to reaction at 120° C. for 12 hours, giving Compound 3 as a white solid at a yield of 43%. Compound 3 is the novel phenanthrene compound of the present invention. $^1$H NMR (CDCl$_3$): δ (ppm) 1.41–1.49(m, 8H), about 1.7(m, 2H), 1.99–2.06(m, 4H), 2.06–2.20(m, 4H), 4.03–4.11(m, 4H), 6.96–6.78(d, 2H), 7.40–7.46(m, 4H), 7.54–7.56(d, 2H), 8.13(s, 2H).

UV: λ$_{max}$ 327 nm. PL: λ$_{max}$ 385 nm.

The following reaction scheme illustrates the preparation of Compound 3:

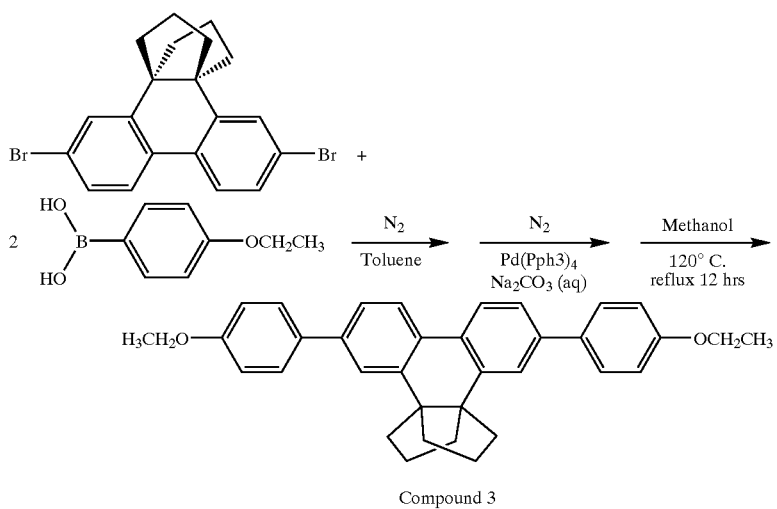

Compound 3

Example 4

Synthesis of 9,10:9,10-bis(trimethylene)-2,7-bis(4-t-butylphenyl)-9,10-dihydrophenanthrene Under nitrogen, 1 ml 2M sodium carbonate aqueous solution, Pd(Pph$_3$)$_4$ as a catalyst, and Aliquat 336 as a phase transfer catalyst were added to 0.5 grams of 4-t-butylphenylboronic acid (manufactured by Lancaster Co., 97%) and 0.31 grams of Compound 2 in 25 ml toluene with the product refluxed to reaction at 120° C. for 12 hours, giving Compound 4 as a white solid at a yield of 36%. $^1$H NMR (CDCl$_3$): 6 (ppm) 1.54(s, 18H), 1.42–1.58(m, 2H), 1.62–1.78(m, 2H), 1.98–2.10(m, 4H), 2.15–2.22(m, 4H), 7.44–7.49(m, 8H), 7.57–7.6(d, 4H), 8.16–8.17(d, 2H).

The following reaction scheme illustrates the preparation of Compound 4:

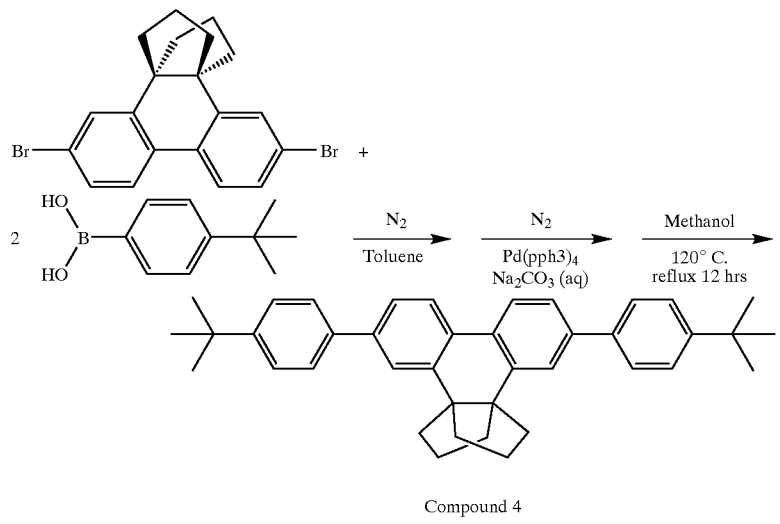

Compound 4

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A phenanthrene compound of formula (I)

Formula (I)

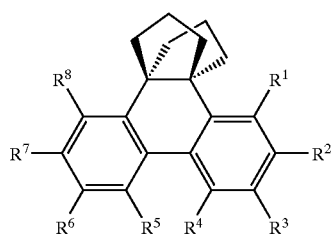

wherein, each R$^1$, R$^2$, R$^3$, R$^4$, R$^5$, R$^6$, R$^7$, and R$^8$ is independently hydrogen, halogen, C$_{1-6}$ is alkyl, C$_{1-6}$ alkoxy, or a conjugated group wherein the conjugated group is a substituted or unsubstituted phenyl, substituted or unsubstituted heterocyclic group, substituted or unsubstituted polycyclic phenyl, substituted or unsubstituted polycyclic heterocyclic group.

2. The phenanthrene compound as claimed in claim 1, wherein one of R$^1$, R$^2$, R$^3$, R$^4$, R$^5$, R$^6$R$^7$, and R$^8$ is a conjugated group.

3. The phenanthrene compound as claimed in claim 1, wherein the conjugated group is:

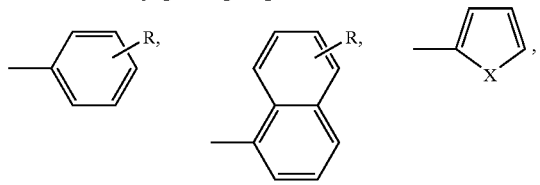

-continued

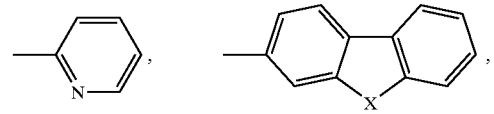

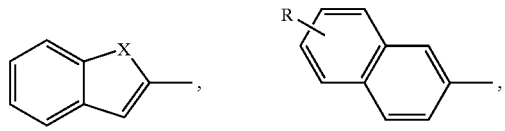

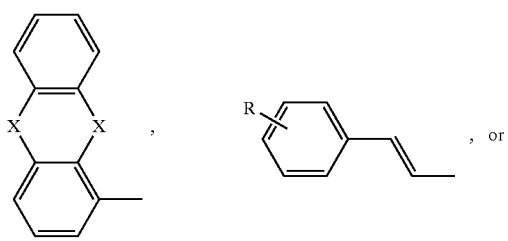

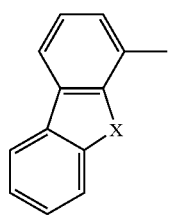

wherein R is $C_{1-6}$ alkyl or $C_{1-6}$ alkoxy, and X is S, O, or N.

4. The phenanthrene compound as claimed in claim 2, wherein $R^2$ or $R^7$ is

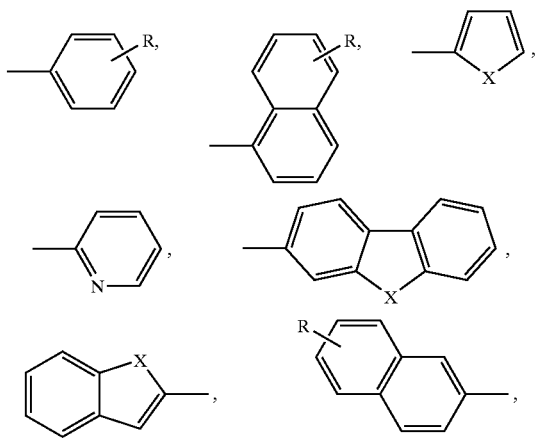

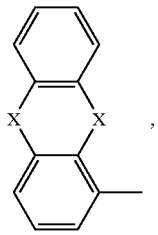

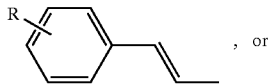

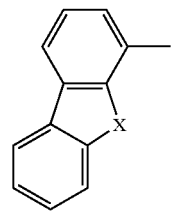

wherein R is $C_{1-6}$ alkyl or $C_{1-6}$ alkoxy, and X is S, O, or N.

5. The phenanthrene compound as claimed in claim 4, wherein $R^1$, $R^3$, $R^4$, $R^5$, $R^6$, and $R^8$ are hydrogen.

6. The phenanthrene compound as claimed in claim 5, wherein $R^2$ and $R^7$ are each halogen.

7. The phenanthrene compound as claimed in claim 6, wherein $R^2$ and $R^7$ are each bromine.

8. The phenanthrene compound as claimed in claim 5, wherein $R^2$ and $R^7$ are each naphthyl.

9. The phenanthrene compound as claimed in claim 5, wherein $R^2$ and $R^7$ are each ethoxyphenyl.

10. The phenanthrene compound as claimed in claim 5, wherein $R^2$ and $R^7$ are each butylphenyl.

* * * * *